United States Patent
Chen et al.

(10) Patent No.: US 10,365,219 B1
(45) Date of Patent: Jul. 30, 2019

(54) TWO-MODE RAMAN OPTICAL PROJECTION TOMOGRAPHY SYSTEM

(71) Applicant: Xidian University, Xi'an (CN)

(72) Inventors: Xueli Chen, Xi'an (CN); Yonghua Zhan, Xi'an (CN); Nan Wang, Xi'an (CN); Honghao Cao, Xi'an (CN); Duofang Chen, Xi'an (CN); Shouping Zhu, Xi'an (CN); Jimin Liang, Xi'an (CN)

(73) Assignee: XIDIAN UNIVERSITY, Xi'an (CN)

( * ) Notice: Subject to any disclaimer, the term of this patent is extended or adjusted under 35 U.S.C. 154(b) by 0 days.

(21) Appl. No.: 16/258,703

(22) Filed: Jan. 28, 2019

Related U.S. Application Data

(63) Continuation of application No. PCT/CN2018/084672, filed on Apr. 26, 2018.

(30) Foreign Application Priority Data

Feb. 6, 2018 (CN) .......................... 2018 1 0118807

(51) Int. Cl.
   *G01J 3/44* (2006.01)
   *G01N 21/64* (2006.01)
   *G01N 21/47* (2006.01)
   *G01N 21/17* (2006.01)

(52) U.S. Cl.
   CPC ..... *G01N 21/6486* (2013.01); *G01N 21/4795* (2013.01); *G01N 21/6458* (2013.01); *G01N 2021/1787* (2013.01)

(58) Field of Classification Search
   CPC ...... G01J 3/02; G01J 3/44; G01J 3/45; G01N 21/64; G01N 21/65; G01N 21/47; G02B 9/02; G02B 21/00
   See application file for complete search history.

(56) References Cited

U.S. PATENT DOCUMENTS

2014/0085623 A1   3/2014   Lorbeer et al.
2017/0325896 A1*  11/2017  Donhowe ............. G06F 19/321

FOREIGN PATENT DOCUMENTS

| CN | 102499639 A | 6/2012 |
| CN | 104204898 A | 12/2014 |
| CN | 105874317 A | 8/2016 |
| WO | 2013132257 A1 | 9/2013 |
| WO | 2016020684 A1 | 2/2016 |

* cited by examiner

*Primary Examiner* — Abdullahi Nur
(74) *Attorney, Agent, or Firm* — Gokalp Bayramoglu

(57) ABSTRACT

The invention discloses a two-mode Raman optical projection tomography system. Samples are irradiated by the laser beam after the beam being expanded by beam expander. Optical signal of each mode will be separated by the beam splitter. Sparse sampling method is used for signal collection. Optical transmission projection signal acquisition module collects transmitted light of samples to form optical projection image. Multi-spectral Raman scattering signal acquisition module collects Raman scattering light produced by samples. Background noise is removed from the collected data. Sparse sampling data are reconstructed by using algebraic reconstruction method (ART) based on TV minimization. The three-dimensional structure image obtained by reconstruction and the three-dimensional chemical compositions image are fused to obtain the three-dimensional volume image with multiple information.

14 Claims, 2 Drawing Sheets

TWO-MODE RAMAN OPTICAL PROJECTION TOMOGRAPHY SYSTEM

CROSS REFERENCE TO RELATED APPLICATIONS

This application is the continuation application of International Application No. PCT/CN2018/084672, filed on Apr. 26, 2018, which is based upon and claims priority to Chinese Application No. 2018101188073, filed on Feb. 6, 2018, the entire contents of which are incorporated herein by reference.

TECHNICAL FIELD

The invention belongs to the technical field of testing or analyzing materials by means of measuring the chemical or physical properties of materials, particularly relates to a two-mode Raman optical projection tomography system.

BACKGROUND

Currently, the existing technology commonly used in the industry is as follows: volumetric imaging can achieve quantitative and global measurement of complex systems, and is crucial in the research of cell metabolism, brain function and developmental biology. The simplest way to achieve volumetric imaging is to collect two-dimensional images with laser scanning in two-dimensional plane by means of optical sectioning scanning, so that the laser focus moves along the axial direction to obtain three-dimensional image information. In this method, high ability of the laser beam focus axial sectioning is required. Both confocal fluorescence microscopy and coherent Raman scattering microscopy have this ability. However, these sectioning methods have very strict requirements for sample size and are time-consuming for samples with thickness of several hundred microns. Light sheet microscopy overcomes the problem of time-consumption by broadening the laser beam into a thin plane, then scanning the sample by the thin plane and collecting images in a direction which is at 90 degrees to the direction of the laser beam to realize three-dimensional imaging of the entire volume of the sample. Light sheet fluorescence microscopy has achieved high resolution and high-speed volumetric imaging of biological samples from single cells to whole embryos. Although this method has been widely used, the fluorescent labels used in the imaging process may cause some serious problems, such as strong disturbance of biological system function, nonspecific targeting, cytotoxicity, etc. Raman light sheet microscopy based on spontaneous Raman effect can perform label-free volumetric imaging and avoid the problems caused by fluorescent labeling. However, in light sheet microscopy technology, the image quality usually degenerates with the distance from the sample surface to the objective lens. Another method of volumetric imaging is tomography, which collects transmission projection images of samples at different angles and reconstructs three-dimensional volume information by using angle-related images. Optical Projection Tomography (OPT) can produce isotropic high-resolution images of three-dimensional samples by light transmission or fluorescence emission. However, there is no contrast of chemical compositions in OPT of light transmission, and OPT for fluorescence emission is also limited to the problem of fluorescent labeling. Spontaneous Raman tomography was proposed by fusion of spontaneous Raman imaging with diffuse optical tomography, which can perform three-dimensional imaging of chemical compositions of samples, but its spatial resolution is low and the imaging speed is relative slow. In order to solve this problem, based on Bessel beam, stimulated Raman projection tomography is proposed by combining stimulated Raman scattering microscopy and projection tomography technology, which can achieve label-free volumetric imaging with micron-scale resolution and better speed. However, this method is unable to achieve a better three-dimensional imaging effect for large scale samples and provide the structural image information of samples. Although there are many methods available to achieve volumetric imaging of samples, these methods are either limited by the problem of fluorescent labeling or imaging performance, and these methods can only provide single information of the structure or chemical compositions, and cannot obtain multi-mode image information at the same time.

To sum up, the existing technology has the following problems: the existing technology for achieving volumetric imaging of samples is limited by fluorescent labeling and imaging performance, which can only provide single information of the structure or chemical compositions, and cannot obtain multi-mode image information at the same time. 1. The influence of fluorescent labels. The fluorescent labels used in the current imaging process may cause some serious problems, such as strong disturbance of biological system function, nonspecific targeting, cytotoxicity, etc.; 2. the imaging scale is small, and currently the way capable of label-free three-dimensional imaging is generally only a few hundred microns; 3. the imaging process only obtains single information. Either the structural images can be obtained and the functional changes of molecules cannot be seen, or the functional images without labels can be obtained, but the structure and location information cannot be determined.

Difficulty and significance of solving the above technical problems are as follows:

Difficulty: how to obtain the fusion image of the structure and chemical compositions of large scale samples at the same time with a label-free manner;

Significance: impacts of fluorescent labels on biological systems can be avoided by label-free way; large scale imaging method can be used to image micron-scale samples to obtain images with micron resolution; at the same time, the structure and chemical compositions imaging ensure that the high fit fusion of the two kinds of information, so as to obtain more comprehensive information of the sample.

SUMMARY

The technical problems to be solved by the present invention is to provide a two-mode Raman optical projection tomography system.

The present invention is realized as follows. A two-mode Raman optical projection tomography method, the two-mode Raman optical projection tomography method includes:

step 1, irradiating samples by the laser beam after the laser beam being expanded by beam expander; separating optical signal of each mode by a beam splitter; using sparse sampling method for signal collection, collecting, by optical transmission projection signal acquisition module, transmitted light of samples to form optical projection image; and collecting Raman scattering light produced by samples by multi-spectral Raman scattering signal acquisition module;

step 2: removing the background noise from the collected data; using a set of bright field data and dark field data collected before the formal data collection for bright field correction and dark field correction of the collected data;

step 3: reconstructing sparse sampling data by TV (Total Variation) minimization based Algebraic Reconstruction Technique (ART) algorithm;

step 4. fusing the three-dimensional structure image and the three-dimensional image of chemical compositions obtained by the reconstruction to obtain the three-dimensional volumetric image with multiple information.

Further, the step 3 specifically includes:

(1) initializing images of the collected data to determine an initial value $\vec{f}=0$ and letting $\vec{f}_0=\vec{f}$; wherein f represents the reconstructed image;

(2) using the distance driven projection model for an ART iterative reconstruction:

$$\vec{f}^{(k+1)} = \vec{f}^{(k)} + \lambda \vec{W}_i \frac{g_i - \vec{W}_i \cdot \vec{f}^{(k)}}{\vec{W}_i \cdot \vec{W}_i}$$

wherein $g_i$ is the projection value of the $i^{th}$ ray; $\vec{W}_i$ is weight of the contribution of the pixels to the $i^{th}$ ray; k is the current iterative number; $\lambda$ is the relaxation factor;

(3) applying nonnegative constraints to the reconstructed image:

$$f_j = 0, \text{ if } f_j < 0;$$

(4) calculating $d_{img} = |\vec{f} - \vec{f}_0|$; wherein $d_{img}$ represents difference between the two reconstructed images;

(5) using the method of steepest descent to calculate the gradient descent direction $\vec{d}$ and unit vector $\hat{d}$ of the whole image, and using TV minimization calculation to update the image:

$$\vec{f} = \vec{f} - \lambda_{TV} d_{img} \hat{d};$$

(6) letting $\vec{f}_0 = \vec{f}$;

(7) determining whether iteration operation meets the stop condition, if yes, stopping the iteration operation; otherwise, going to (2) for the next iteration operation until the stop condition is met.

The stop condition comprises a predetermined number of the times of the iteration and the predetermined value of $d_{img}$. Such as if the value of $d_{img}$ is less than the predetermined value, the iteration operation stops.

Another purpose of the invention is to provide a two-mode Raman optical projection tomography system for the two-mode Raman optical projection tomography method. The two-mode Raman optical projection tomography system comprises:

light source module, which is configured to provide high quality, low noise and stable wide beam light source for the two-mode imaging system;

carrier control module, which is configured to provide four degrees of freedom movement operations along XYZ axis and rotation for the sample. It is configured to adjust the appropriate position of the sample in the imaging field and rotate the sample to obtain multi-angle projection images.

signal separation module, which is configured for separating multi-spectral Raman scattering signal and transmission projection signal.

multi-spectral Raman scattering signal acquisition module, which is configured to collect Raman scattering light generated by samples.

optical transmission projection signal acquisition module, which is configured to collect the transmitted light of laser beam that passes through the sample and forms optical projection image;

system control and data processing module, which is configured for the control of the light source module, the carrier control module, the multi-spectral Raman scattering signal acquisition module and the optical transmission projection signal acquisition module, as well as the transformation of the obtained multi-spectral Raman scattering signal and transmission projection signal into two-dimensional images for processing and analyzing to achieve volumetric imaging.

Further, the light source module comprises a continuous-wave laser, a laser beam quality optimizer and laser beam expander;

the continuous-wave laser is 620 nm semiconductor laser. The laser beam quality optimizer and laser beam expander are a 4F system consisting of two lenses and a spatial filter.

Further, the carrier control module comprises XYZ three-axis electronic control translation stage, sample carrier platform, sample holder and stepping motor;

XYZ three-axis electronic control translation stage and stepping motor are connected with the computer processing unit. XYZ three-axis electronic control translation stage is controlled to adjust the position of the sample in space and the stepping motor is controlled to drive the sample holder.

Further, the multi-spectral Raman scattering signal acquisition module comprises a collection lens, a wavelength tunable filter, an imaging lens and a flat panel detector which are arranged in sequence;

the multi-spectral Raman scattering light separated by signal separation module is collected through collecting lens, then is focused and passed to the wavelength tunable filter to perform spectral separation of different wavelengths, and passed by the imaging lens to the sensitive surface of flat panel detector for transforming the light signal into electrical signal and sending the electrical signal to the system control and data processing module for data storage and processing.

Further, the optical transmission projection signal acquisition module comprises a collection lens, a magnifying objective lens, a band-pass filter and a flat panel detector which are arranged in sequence;

the optical transmission projection signal separated by signal separation module is collected through the collecting lens, then is magnified by the magnifying objective lens, to filter out stray light by the band-pass filter and then passed to the sensitive surface of flat panel detector for transforming the light signal into electrical signal, and the electrical signal is sent to the system control and data processing module for data storage and processing.

Further, the system control and data processing module comprises an image acquisition card and a computer processing unit;

the image acquisition card is connected to the flat panel detector, and the computer processing unit is connected with the carrier control module.

Another purpose of the invention is to provide a bio-optical imaging system applying the two-mode Raman optical projection tomography method.

To sum up, the advantages and technical effects of the invention are as follows:

(1) Triple information. Three-dimensional chemical composition information and Raman spectrum information of the sample can be obtained through the multi-spectral Raman scattering signal channel, and the three-dimensional structure information of the sample can be obtained through the optical transmission projection signal channel at the same time. Therefore, the two-mode imaging system of the invention can obtain the triple information of the sample at the same time.

(2) High compatibility. Since the same imaging system is used to realize multi-spectral Raman image and optical transmission projection image, the three-dimensional information of chemical compositions obtained by the two-mode imaging system of the invention has a higher fit with the three-dimensional structure information, and the image fusion can be carried out more easily in the later image processing process.

(3) High imaging speed of large scale samples. The existing three-dimensional Raman spectroscopic imaging technology is difficult to realize large scale sample imaging. The two-mode imaging system of the invention can realize the simultaneous imaging of the three-dimensional structure and chemical compositions of micron-level samples. Combined with sparse sampling and reconstruction method, label-free rapid volumetric imaging can be achieved.

(4) Simple system. The present invention uses a spectroscope and a filter to realize the separation of the two modal data, making the simultaneous imaging of multi-mode more convenient and simple.

The invention skillfully combines Raman spectroscopic imaging and optical projection tomography into the same system, and simultaneously provides triple information and high information fit. With simple structure, fast imaging speed of large scale samples, simple and flexible operation, and being easy to grasp, it has a wide application prospect.

In the figure: 1. light source module; 1-1. continuous-wave laser; 1-2. the laser beam quality optimizer and laser beam expander; 2. the carrier control module; 2-1. three-axis electronic control translation platform; 2-2. sample carrier platform; 2-3. sample holder; 2-4. stepping motor; 3. signal separation module; 4. the multi-spectral Raman scattering signal acquisition module; 4-1. collection lens; 4-2. wavelength tunable filter; 4-3. imaging lens; 4-4. flat panel detector; 5. optical transmission projection signal acquisition module; 5-1. collection lens; 5-2. magnifying objective lens; 5-3. band-pass filter; 5-4. flat panel detector; 6. system control and data processing module; 6-1. image acquisition card; 6-2. computer processing unit.

DETAILED DESCRIPTION OF THE EMBODIMENTS

In order to make the purpose, technical solution and advantages of the invention clear, the present invention is further described in detail with the help of following embodiments. It shall be understood that the specific embodiments described herein are used only to interpret the invention and are not used to limit the invention.

The invention can simultaneously provide distribution image of chemical compositions, structure image and spectral information of chemical compositions of the sample to be tested. The invention provides a two-mode tomography system capable of simultaneously performing Raman spectroscopic imaging and optical projection imaging. Raman spectroscopic imaging can provide the distribution and spectral information of the chemical compositions of samples, and optical projection imaging can provide the structural information of samples, so as to realize simultaneous imaging of the chemical compositions and structural information of samples by using a same system.

Figure 1:
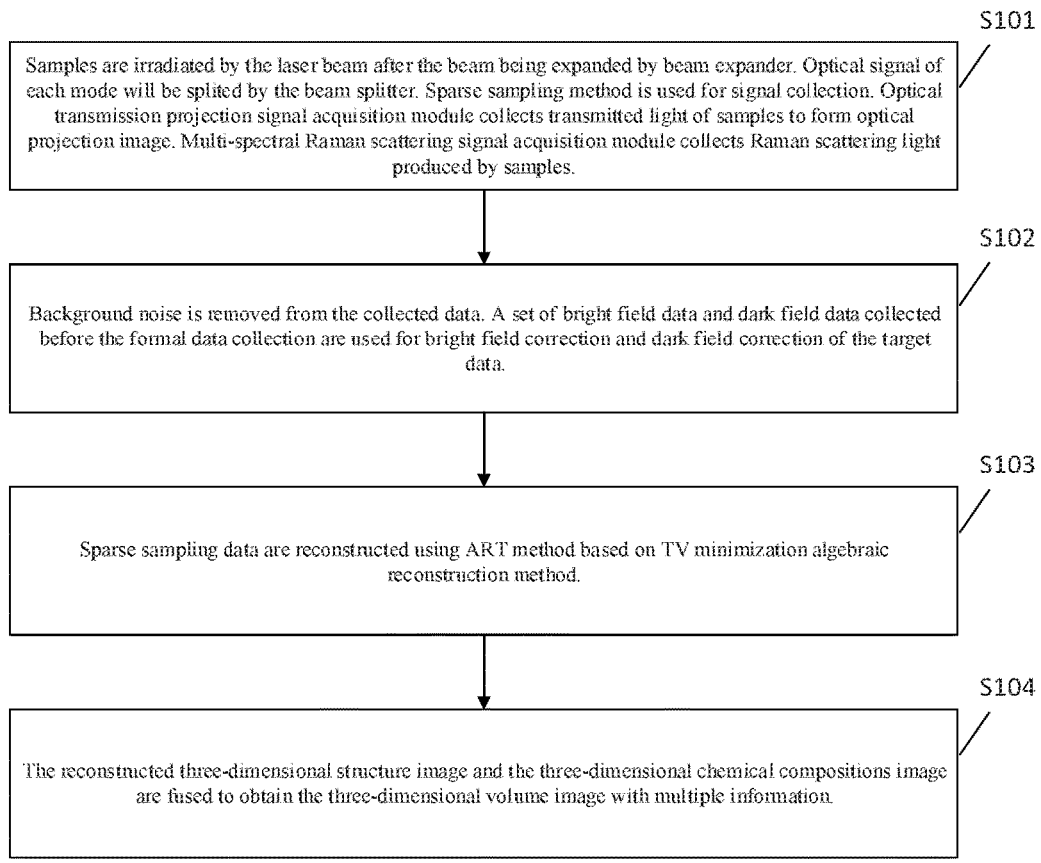
FIG. 1 is a flow chart of the two-mode Raman-optical projection tomography method provided by an embodiment of the present invention.

As shown in FIG. 1, the two-mode Raman optical projection tomography method provided by the embodiment of the invention includes the following steps:

S101: samples are irradiated by the laser beam after the laser beam being expanded by beam expander; optical signal of each mode will be separated by the beam splitter; sparse sampling method is used for signal collection; optical transmission projection signal acquisition module collects transmitted light of samples to form optical projection image; multi-spectral Raman scattering signal acquisition module collects Raman scattering light produced by samples;

S102: background noise is removed from the collected data; a set of bright field data and dark field data collected before the formal data collection are used for bright field correction and dark field correction of the collected data, to reduce the impact on the data by noise fluctuation;

S103: sparse sampling data are reconstructed based on TV minimization based ART algorithm;

S104: the three-dimensional structure image and the three-dimensional image of chemical compositions obtained by the reconstruction are fused to obtain the three-dimensional volume image with multiple information.

Step S103 specifically includes:

(a) initialize images of the collected data to determine an initial value $\vec{f}=0$ and let $\vec{f}_0=\vec{f}$; f represents the reconstructed image;

(b) the distance driven projection model was used for an ART iterative reconstruction:

$$\vec{f}^{(k+1)} = \vec{f}^{(k)} + \lambda \vec{W}_i \frac{g_i - \vec{W}_i \cdot \vec{f}^{(k)}}{\vec{W}_i \cdot \vec{W}_i}$$

wherein $g_i$ is the projection value of the $i^{th}$ ray; $\vec{W}_i$ is weight of the contribution of the pixels to the $i^{th}$ ray; k is the current iterative number; $\lambda$ is the relaxation factor;

(c) nonnegative constraints are applied to the reconstructed image:

$f_j=0$, if $f_j<0$;

(d) calculate $d_{img}=|\vec{f}-\vec{f}_0|$; $d_{img}$ represents difference between the two reconstructed images;

(e) the method of steepest descent is used to calculate the gradient descent direction $\vec{d}$ and unit vector $\hat{d}$ of the whole image, and TV minimization calculation is carried out to update the image:

$\vec{f}=\vec{f}-\lambda_{TV}d_{img}\hat{d}$;

(f) let $\vec{f}_0 = \vec{f}$;

(g) If iteration operation meets the stop condition, stop the iteration operation; otherwise, go to (2) for the next iteration operation until the stop condition is met.

The stop condition may be a predetermined number of the times of the iteration and/or the predetermined value of $d_{img}$. Such as if the value of $d_{img}$ is less than the predetermined value, the iteration operation stops.

Figure 2:
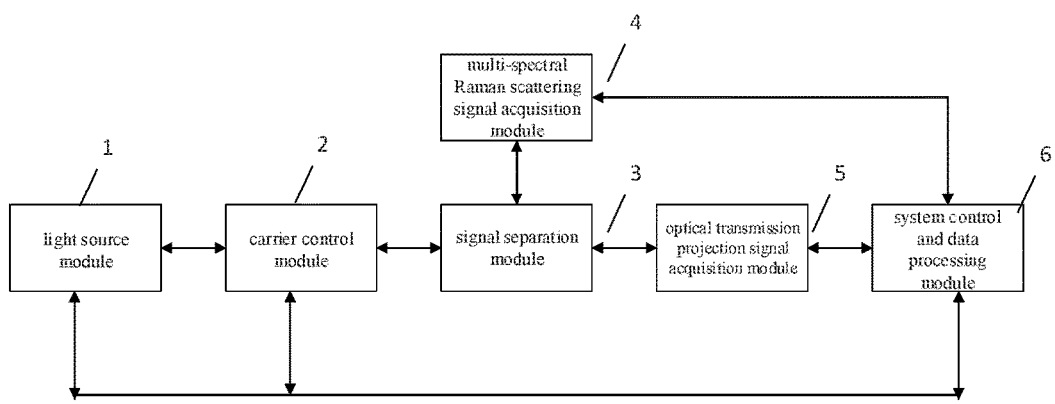
FIG. 2 is a structure diagram of the two-mode Raman-optical projection tomography system provided by the embodiment of the present invention.
Figure 3:
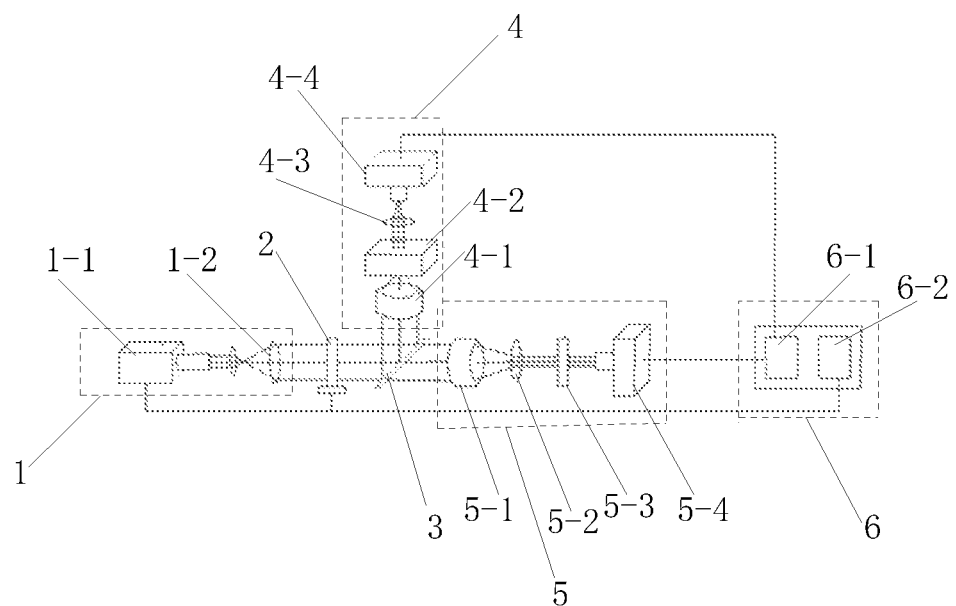
FIG. 3 is a schematic diagram of the two-mode Raman-optical projection tomography system provided by the embodiment of the present invention.
Figure 4:
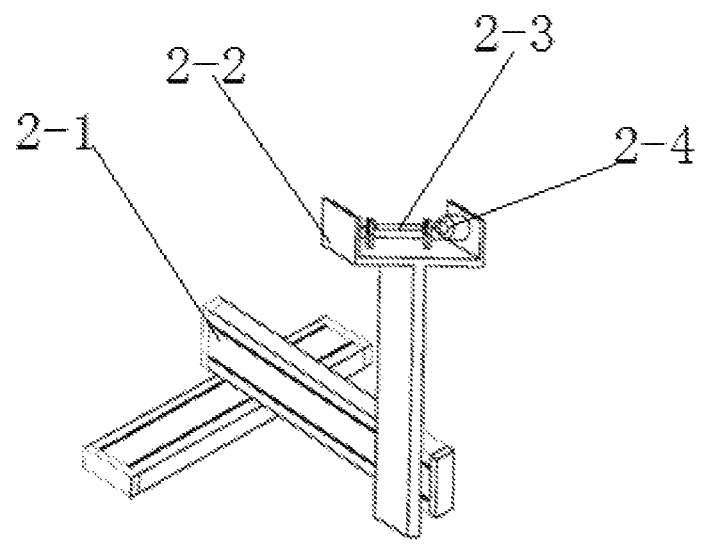
FIG. 4 is a schematic diagram of the carrier apparatus for samples provided by the embodiment of the present invention.

As shown in FIG. 2-FIG. 4, the two-mode Raman optical projection tomography system provided by the embodiment of the present invention includes:

Light source module 1, which is used to provide high quality, low noise and stable wide beam light source for the two-mode imaging system. The light source module 1 includes a continuous-wave laser 1-1, a laser beam quality optimizer and laser beam expander 1-2. The continuous-wave laser 1-1 is 620 nm semiconductor laser. The laser beam quality optimizer and laser beam expander 1-2 are a 4F system consisting of two lenses and a spatial filter.

Carrier control module 2, which is used to provide four degrees of freedom movement operations along XYZ directions and rotation for the sample. It is used to adjust the appropriate position of the sample in the imaging field and rotate the sample to obtain multi-angle projection images;

Signal separation module 3, which is used for separating multi-spectral Raman scattering signal and transmission projection signal. Signal separation module 3 is a shortpass dichroic mirror with cut-off wavelength of 620 nm.

Multi-spectral Raman scattering signal acquisition module 4, which is used to collect Raman scattering lights generated by samples.

The multi-spectral Raman scattering signal acquisition module 4 includes collection lens 4-1, wavelength tunable filter 4-2, imaging lens 4-3 and a flat panel detector 4-4 which are arranged in sequence. The multi-spectral Raman scattering light separated by signal separation module 3 is collected by collecting lens 4-1, then is focused and passed to the wavelength tunable filter 4-2 to perform spectral separation of different wavelengths, and passed by the imaging lens to the sensitive surface of flat panel detector 4-4 for transforming the light signal into electrical signal and the electrical signal is sent to the system control and data processing module 6 for data storage and processing. The wavelength tunable filter 4-2 is an acousto-optic tunable filter.

Optical transmission projection signal acquisition module 5, which is used to collect the transmitted light of laser beam that passes through the sample and forms optical projection image. The optical transmission projection signal acquisition module 5 comprises collection lens 5-1, magnifying objective lens 5-2, band-pass filter 5-3 and flat panel detector 5-4 which are arranged in sequence. Wherein, the optical transmission projection signal separated by signal separation module 3 is collected through the collecting lens 5-1, then is magnified by the magnifying objective lens 5-2, to filter out stray light by the band-pass filter 5-3 and then passed to the sensitive surface of flat panel detector 5-4, to transform the light signal into electrical signal and send the electrical signal to the system control and data processing module 6 for data storage and processing.

The flat panel detector 4-4 and the flat panel detector 5-4 are EMCCD cameras.

System control and data processing module 6, which is used for the control of light source module 1, the carrier control module 2, the multi-spectral Raman scattering signal acquisition module 4 and the transmission projection signal acquisition module 5, as well as the transformation of the obtained electrical signals into two-dimensional images for processing and analysis to achieve volumetric imaging.

The system control and data processing module 6 comprises image acquisition card 6-1 and computer processing unit 6-2. Wherein, the image acquisition card 6-1 is connected to the flat panel detector 4-4 and the flat panel detector 5-4. The computer processing unit 6-2 and carrier control module 2 are connected.

FIG. 4 is the schematic diagram of the carrier control module 2 used in the invention, which comprises XYZ three-axis electronic control translation stage 2-1, sample carrier platform 2-2, sample holder 2-3 and stepping motor 2-4. XYZ three-axis electronic control translation stage 2-1 and stepping motor 2-4 are connected with the computer processing unit 6-2. XYZ three-axis electronic control translation stage 2-1 is controlled to adjust the position of the sample in space and the stepping motor 2-4 is controlled to drive the sample holder 2-3 to make the sample rotate at a precise angle in space.

The foregoing is only a preferred embodiment of the invention and does not limit the invention. Any modification, equivalent replacement and improvement made within the spirit and principles of the invention shall be included in the protection scope of the invention.

We claim:

1. A two-mode Raman optical projection tomography system, comprising:

light source module: wherein the light source module is configured to provide wide beam light source for the two-mode Raman optical projection tomography system;

carrier control module: wherein the carrier control module is configured to provide four degrees of freedom movement operations along XYZ directions and rotation for a sample, to adjust a position of the sample in an imaging field and rotate the sample to obtain multi-angle projection images;

signal separation module: wherein the signal separation module is configured for separating multi-spectral Raman scattering signal and transmission projection signal;

multi-spectral Raman scattering signal acquisition module: wherein the multi-spectral Raman scattering signal acquisition module is configured to collect Raman scattering light generated by the sample;

optical transmission projection signal acquisition module: wherein the optical transmission projection signal acquisition module is configured to collect transmitted light of a laser beam that passes through the sample and form an optical projection image;

system control and data processing module: wherein the system control and data processing module is configured for the control of the light source module, the carrier control module, the multi-spectral Raman scattering signal acquisition module and the transmission projection signal acquisition module, and a transformation of obtained the multi-spectral Raman scattering signal and the transmission projection signal into two-dimensional images for processing and analyzing to achieve volumetric imaging.

2. The two-mode Raman optical projection tomography system of claim 1, wherein the light source module comprises a continuous-wave laser, a laser beam quality optimizer and laser beam expander;

the continuous-wave laser is 620 nm semiconductor laser and the laser beam quality optimizer and beam expander is a 4F system consisting of two lenses and a spatial filter.

3. The two-mode Raman optical projection tomography system of claim 1, wherein the carrier control module comprises a three-axis electronic control translation stage, a sample carrier platform, a sample holder and a stepping motor;

the three-axis electronic control translation stage and the stepping motor are connected with a computer processing unit of the system control and data processing module; the three-axis electronic control translation stage is controlled to adjust the position of the sample in space and the stepping motor is controlled to drive the sample holder.

4. The two-mode Raman optical projection tomography system of claim 1, wherein the multi-spectral Raman scattering signal acquisition module comprises a collecting lens, a wavelength tunable filter, an imaging lens and a flat panel detector which are arranged in sequence;

the multi-spectral Raman scattering light separated by the signal separation module is collected by the collecting lens, then is focused and passed to the wavelength tunable filter to perform spectral separation of different wavelengths, and passed by the imaging lens to a sensitive surface of flat panel detector, a light signal is transformed into an electrical signal and the electrical signal is sent to the system control and data processing module for data storage and processing.

5. The two-mode Raman optical projection tomography system of claim 1, wherein the optical transmission projection signal acquisition module comprises a collection lens, a magnifying objective lens, a band-pass filter and a flat panel detector which are arranged in sequence;

the optical transmission projection signal separated by the signal separation module is collected by the collecting lens, then is magnified by the magnifying objective lens, and transmitted to filter out stray light by the band-pass filter and then passed to a sensitive surface of the flat panel detector, for transforming a light signal into an electrical signal and sending the electrical signal to the system control and data processing module for data storage and processing.

6. The two-mode Raman optical projection tomography system of claim 1, wherein the system control and data processing module comprises an image acquisition card and a computer processing unit;

the image acquisition card is connected to a flat panel detector of the multi-spectral Raman scattering signal acquisition module and a flat panel detector of the optical transmission projection signal acquisition module; and the computer processing unit is connected with the carrier control module.

7. A two-mode Raman optical projection tomography method of the two-mode Raman-optical projection tomography system of claim 1, comprising the following steps:

step 1, irradiating the sample by the laser beam after the laser beam being expanded by a laser beam expander; separating optical signal of each mode by a beam splitter; using sparse sampling method for signal collection; collecting transmitted light of the sample by the optical transmission projection signal acquisition module to form the optical projection image; collecting, by multi-spectral Raman scattering signal acquisition module, the Raman scattering light generated by the sample;

step 2: removing the background noise from a collected data; collecting a set of bright field data and dark field data before a formal data collection for bright field correction and dark field correction of the collected data;

step 3: reconstructing sparse sampling data by Total Variation (TV) minimization based Algebraic Reconstruction Technique (ART) algorithm;

step 4: fusing a three-dimensional structure image and a three-dimensional image of chemical compositions obtained by the reconstruction to obtain the three-dimensional volume image with multiple information.

8. The two-mode Raman optical projection tomography method of the claim 7, wherein the step 3 specifically comprises:

(1) initializing an image of the collect data to determine an initial value $\vec{f}=0$ and letting $\vec{f}_0=\vec{f}$; wherein f represents the reconstructed image;

(2) reconstructing an ART iterative by using a distance driven projection model:

$$\vec{f}^{(k+1)} = \vec{f}^{(k)} + \lambda \vec{W}_i \frac{g_i - \vec{W}_i \cdot \vec{f}^{(k)}}{\vec{W}_i \cdot \vec{W}_i}$$

wherein $g_i$ is the projection value of the $i^{th}$ ray; $\vec{W}_i$ is weight of the contribution of the pixels to the $i^{th}$ ray; k is the current iterative number; $\lambda$ is the relaxation factor;

(3) applying nonnegative constraints to a reconstructed image:

$f_j=0$, if $f_j<0$;

(4) calculating $d_{img}=|\vec{f}-\vec{f}_0|$; $d_{img}$ represents difference between the two reconstructed images;

(5) calculating the gradient descent direction $\vec{d}$ and unit vector $\hat{d}$ of the currently reconstructed image by using the method of steepest descent, and updating the currently reconstructed image by the TV minimization calculation:

$$\vec{f}=\vec{f}-\lambda_{TV}d_{img}\hat{d};$$

(6) letting $\vec{f}_0=\vec{f}$;

(7) determining if an iteration operation meets a stop condition, if so, stopping the iteration operation; otherwise, going to (2) for a next iteration operation until the stop condition is met.

9. A bio-optical imaging system, comprising the two-mode Raman optical projection tomography system of claim 1.

10. The bio-optical imaging system of claim 9, wherein the light source module comprises a continuous-wave laser, a laser beam quality optimizer and laser beam expander;

the continuous-wave laser is 620 nm semiconductor laser and the laser beam quality optimizer and laser beam expander is a 4F system consisting of two lenses and a spatial filter.

11. The bio-optical imaging system of claim 9, wherein the carrier control module comprises a three-axis electronic control translation stage, a sample carrier platform, a sample holder and a stepping motor;

the three-axis electronic control translation stage and the stepping motor are connected with a computer processing unit of the system control and data processing module; the three-axis electronic control translation stage is controlled to adjust the position of the sample in space and the stepping motor is controlled to drive the sample holder.

12. The bio-optical imaging system of claim 9, wherein the multi-spectral Raman scattering signal acquisition module comprises a collecting lens, a wavelength tunable filter, an imaging lens and a flat panel detector which are arranged in sequence;

the multi-spectral Raman scattering light separated by the signal separation module is collected by the collecting lens, then is focused and passed to the wavelength tunable filter to perform spectral separation of different wavelengths, and passed by the imaging lens to a sensitive surface of flat panel detector, a light signal is transformed into an electrical signal and the electrical signal is sent to the system control and data processing module for data storage and processing.

13. The bio-optical imaging system of claim 9, wherein the optical transmission projection signal acquisition module comprises a collection lens, a magnifying objective lens, a band-pass filter and a flat panel detector which are arranged in sequence;

the optical transmission projection signal separated by the signal separation module is collected by the collecting lens, then is magnified by the magnifying objective lens, and transmitted to filter out stray light by the band-pass filter and then passed to a sensitive surface of the flat panel detector, for transforming a light signal into an electrical signal and sending the electrical signal to the system control and data processing module for data storage and processing.

14. The bio-optical imaging system of claim 9, wherein the system control and data processing module comprises an image acquisition card and a computer processing unit;

the image acquisition card is connected to a flat panel detector of the multi-spectral Raman scattering signal acquisition module and a flat panel detector of the optical transmission projection signal acquisition module; and the computer processing unit is connected with the carrier control module.

* * * * *